(12) United States Patent
Eichler et al.

(10) Patent No.: US 9,427,172 B2
(45) Date of Patent: Aug. 30, 2016

(54) ROLL DETECTION AND SIX DEGREES OF FREEDOM SENSOR ASSEMBLY

(75) Inventors: Uzi Eichler, Haifa (IL); Alon Izmirli, Ganot Hadar (IL); Dan Seter, Haifa (IL)

(73) Assignee: MediGuide Ltd., Haifa (IL)

( * ) Notice: Subject to any disclaimer, the term of this patent is extended or adjusted under 35 U.S.C. 154(b) by 760 days.

(21) Appl. No.: 13/341,396

(22) Filed: Dec. 30, 2011

(65) Prior Publication Data

US 2013/0169272 A1 Jul. 4, 2013

(51) Int. Cl.
| | |
|---|---|
| *G01R 33/04* | (2006.01) |
| *A61B 5/06* | (2006.01) |
| *A61B 6/12* | (2006.01) |
| *A61B 6/00* | (2006.01) |
| *A61B 8/08* | (2006.01) |

(52) U.S. Cl.
CPC ............. *A61B 5/062* (2013.01); *A61B 6/12* (2013.01); *A61B 6/487* (2013.01); *A61B 8/0841* (2013.01); *A61B 2090/3782* (2016.02)

(58) Field of Classification Search
None
See application file for complete search history.

(56) References Cited

U.S. PATENT DOCUMENTS

| | | | |
|---|---|---|---|
| 6,201,387 B1 | 3/2001 | Govari | |
| 6,233,476 B1 | 5/2001 | Strommer et al. | |
| 6,253,770 B1 * | 7/2001 | Acker et al. | 128/899 |
| 6,498,944 B1 | 12/2002 | Ben-Haim et al. | |
| 6,593,884 B1 | 7/2003 | Gilboa et al. | |
| 6,615,155 B2 | 9/2003 | Gilboa | |
| 6,788,967 B2 | 9/2004 | Ben-Haim et al. | |
| 7,197,354 B2 | 3/2007 | Sobe | |
| 7,386,339 B2 | 6/2008 | Strommer et al. | |
| 7,816,915 B2 | 10/2010 | Susel et al. | |
| 8,611,984 B2 | 12/2013 | Greenburg et al. | |
| 8,644,907 B2 * | 2/2014 | Hartmann et al. | 600/424 |
| 2003/0187347 A1 * | 10/2003 | Nevo | A61B 5/06 600/424 |
| 2006/0025678 A1 | 2/2006 | Speier et al. | |
| 2009/0163810 A1 | 6/2009 | Kanade et al. | |
| 2010/0210939 A1 | 8/2010 | Hartmann et al. | |
| 2010/0324412 A1 | 12/2010 | Govari et al. | |
| 2012/0172716 A1 | 7/2012 | Sela et al. | |

(Continued)

FOREIGN PATENT DOCUMENTS

| | | |
|---|---|---|
| JP | H10507104 A | 7/1998 |
| JP | 2000-121306 A | 4/2000 |

(Continued)

OTHER PUBLICATIONS

"International Search Report and Written Opinion", PCT/IB2012/057418 Apr. 9, 2013.

(Continued)

*Primary Examiner* — Paresh Patel
(74) *Attorney, Agent, or Firm* — Dykema Gossett PLLC

(57) ABSTRACT

A roll-detecting sensor assembly includes a coil extending along and disposed about an axis. The coil comprises one or more portions, with each portion defining a winding angle. At least one of the portions defines a winding angle that is substantially nonzero relative to a line perpendicular to the axis, whereby the projected area of the coil in an applied magnetic field changes as the coil rotates about the axis. As a result, the coil is configured to produce a signal responsive to the magnetic field indicative of the roll of the sensor about the axis. In an embodiment, at least one of the portions defines a winding angle that is at least 2 degrees. In an embodiment, at least one of the portions defines a winding angle that is about 45 degrees.

22 Claims, 7 Drawing Sheets

(56) References Cited

U.S. PATENT DOCUMENTS

2012/0197108 A1* 8/2012 Hartmann et al. ............ 600/424
2013/0066194 A1 3/2013 Seter et al.

FOREIGN PATENT DOCUMENTS

| JP | 2000-506409 A | 5/2000 |
|---|---|---|
| WO | 96/05768 A1 | 2/1996 |
| WO | 97/29680 A1 | 8/1997 |
| WO | WO-03/051192 | 6/2003 |
| WO | 2009/085487 A1 | 7/2009 |

OTHER PUBLICATIONS

Author: , Title: International Search Report and Written Opinion Citation: PCT/IB2012/057418 Publication Date: Apr. 9, 2013.
Japan Patent Office, Office Action, May 31, 2016, p. 3, Japan.

* cited by examiner

ROLL DETECTION AND SIX DEGREES OF FREEDOM SENSOR ASSEMBLY

BACKGROUND OF THE INVENTION a. Field of the Invention

The present disclosure relates generally to an electromagnetic positioning sensor for a medical device, and more specifically to an electromagnetic positioning sensor that can sense roll.

b. Background Art

Medical devices such as guidewires, catheters, introducers and the like with electromagnetic coil position sensors for device navigation are used in various medical procedures in the body. For example, it is known to equip a catheter with multiple coils sufficient to allow a positioning sensor to detect six (6) degrees-of-freedom (DOF), namely, a three-dimensional (3D) position (X, Y, Z) and a 3D orientation (e.g., roll, pitch, yaw) thereof. However, the design of a coil assembly that can provide such functionality provides challenges, particularly with respect to space constraints.

One known electromagnetic position sensor includes a coil wound symmetrically on a tubular core. Such a sensor may be seen by reference to U.S. Pat. No. 7,197,354 entitled "System for Determining the Position and Orientation of a Catheter" issued to Sobe, hereby incorporated by reference in its entirety as though fully set forth herein. Sobe discloses a core that is hollow, symmetric about a central axis, and can be scaled in length, inner diameter, and outer diameter for a particular application. A coil is wound on the core in a desired winding pattern. The coil, like the core, is symmetric about the central axis. The sensor can detect three degrees of position (X, Y, and Z), as well as pitch and yaw, but the coil cannot detect roll (i.e., the rotational position with respect to the axis of the core). Accordingly, a medical device that incorporates a single symmetric sensor coil only senses five (5) DOF, that is, two orientation parameters, in addition to three position parameters. Despite the DOF limitation, there are nonetheless desirable aspects of the above configuration. For example, the configuration uses minimal space and accommodates an open central lumen.

Known solutions for sensing the roll of a medical device generally involve using multiple sensors, each with a single symmetric coil as described above. For example, both U.S. Patent Application Publication No. 2010/0324412, entitled "Catheter With Obliquely-Oriented Coils" and U.S. Pat. No. 6,593,884, entitled "Intrabody Navigation System for Medical Applications", both of which are hereby incorporated by reference in their entireties as though fully set forth herein, teach placing separate sensors in different locations in a medical device with their respective coils oriented at different angles. Such configurations are more expensive and require more space in a medical device than a unitary sensor on a single core.

There is therefore a need for an electromagnetic position sensor that minimizes or eliminates one or more of the problems set forth above.

BRIEF SUMMARY OF THE INVENTION

Various embodiments herein provide a positioning sensor assembly for a medical device that can detect roll without increasing cost by using additional separate sensors, without obstructing the central lumen of the medical device, and without unduly enlarging the medical device. Accordingly, in at least one embodiment, such a sensor assembly may include a coil extending along and disposed about an axis. The coil comprises one or more portions, with each portion defining a winding angle. At least one of the portions defines a winding angle that is substantially nonzero relative to a line perpendicular to the axis, whereby a projected area of the coil in an applied magnetic field changes as the coil rotates about the axis.

In another embodiment, a sensor assembly may include a core extending along an axis having an outer surface and a coil substantially as described above. The coil includes a first portion disposed on the core outer surface and a second portion electrically coupled with the first portion. The first portion defines a first winding angle, and the second portion defines a second winding angle that is different from the first winding angle. At least one of the first winding angle and the second winding angle is substantially nonzero relative to a plane that is perpendicular to the axis. As a result, the coil is configured to produce a signal responsive to an applied magnetic field indicative of at least the roll of the coil about the axis.

In another embodiment, a sensor assembly may comprise a coil extending along and disposed about an axis. The coil may comprise one or more portions, each portion defining a winding angle, wherein at least one of the one or more portions defines a winding angle that is at least about two degrees relative to a line perpendicular to the axis, whereby a projected area of the coil in an applied magnetic field changes as the coil rotates about said axis.

DETAILED DESCRIPTION OF THE INVENTION

Figure 1:
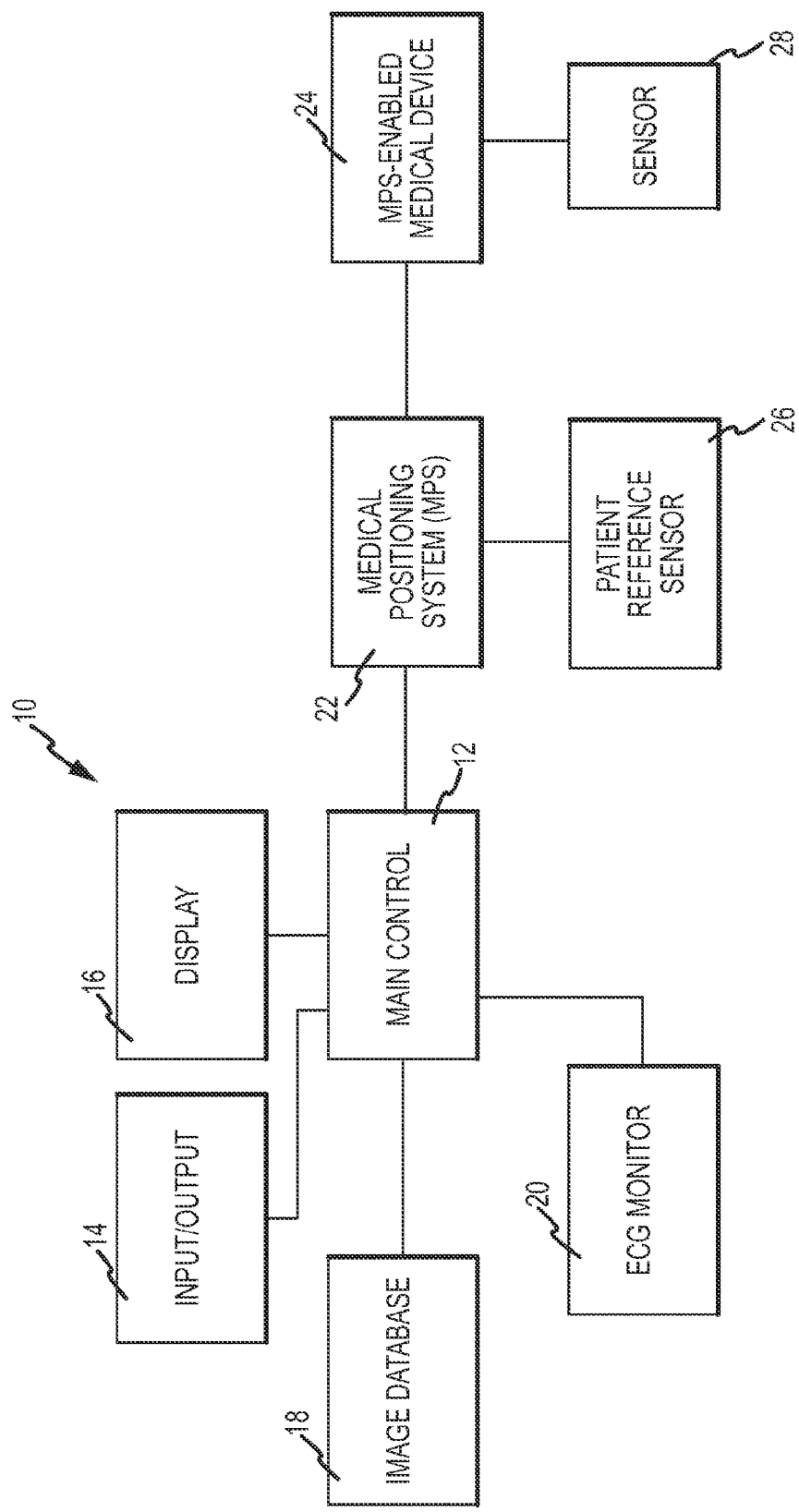
FIG. 1 is a schematic and block diagram view of a system incorporating an embodiment of a position-sensing medical device.

Referring now to the drawings wherein like reference numerals are used to identify identical or similar components in the various views, FIG. 1 is a diagrammatic view of a system 10 in which a medical device, such as a guidewire or catheter, incorporating an electromagnetic position sensor may be used.

Before proceeding to a detailed description of the several electromagnetic positioning sensor embodiments and medical device embodiments of the present invention, a description of an exemplary environment in which such devices and sensors may be used will first be set forth. With continued reference to FIG. 1, system 10 as depicted includes a main electronic control unit 12 (e.g., a processor) having various input/output mechanisms 14, a display 16, an optional image database 18, an electrocardiogram (ECG) monitor 20, a localization system such as a medical positioning system (MPS) 22, an MPS-enabled elongate medical device 24, a patient reference sensor 26, and a roll-sensing MPS location sensor 28.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

MPS 22 is configured to serve as the localization system and therefore to determine positioning (localization) data with respect to one or more MPS location sensors 28 and output a respective location reading. The location readings may each include at least one or both of a position and an orientation (P&O) relative to a reference coordinate system, which may be the coordinate system of MPS 22. For some types of sensors, the P&O may be expressed with five degrees-of-freedom (five DOF) as a three-dimensional (3D) position (i.e., a coordinate in three axes X, Y and Z) and two-dimensional (2D) orientation (e.g., an azimuth and elevation) of a sensor in a magnetic field relative to a magnetic field generator(s) or transmitter(s). For other sensor types, the P&O may be expressed with six degrees-of-freedom (six DOF) as a 3D position (i.e., X, Y, Z coordinates) and 3D orientation (i.e., roll, pitch, and yaw). An exemplary embodiment of an MPS 22 will be described in greater detail below in connection with FIG. 12.

MPS 22 determines respective locations (i.e., P&O) in the reference coordinate system based on capturing and processing signals received from the magnetic field sensor 28 while the sensor is disposed in a controlled low-strength alternating current (AC) magnetic (i.e., electromagnetic) field. It should be noted that although only one sensor 28 is shown, MPS 22 may determine P&O for multiple sensors. As discussed in more detail below, each sensor 28 and the like may comprise a coil and, from an electromagnetic perspective, the changing or AC magnetic field may induce a current in the coil(s) when the coil(s) are in the magnetic field. Sensor 28 is thus configured to detect one or more characteristics (i.e., flux) of the magnetic field(s) in which it is disposed and generate a signal indicative of those characteristics, which is further processed by MPS 22 to obtain a respective P&O for the sensor 28. Depending on the characteristics of sensor 28, the P&O may be expressed with five DOF or with six DOF. Exemplary five-DOF sensors will be described in greater detail below at least in conjunction with FIGS. 6A and 8. Exemplary six-DOF sensors will be described in greater detail below at least in conjunction with FIGS. 7A and 7B.

Referring still to FIG. 1, in an embodiment, MPS 22 may determine the P&O of sensor 28 according to certain physical characteristics of sensor 28 in addition to the signals received from sensor 28. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. MPS 22 may have such characteristics pre-programmed, may determine such characteristics from a calibration procedure, or may receive such characteristics from a storage element coupled with medical device 24.

Position sensor 28 may be associated with MPS-enabled medical device 24. Another MPS sensor, namely, patient reference sensor (PRS) 26 (if provided in system 10) is configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like MPS position sensor 28, PRS 26 is configured to detect one or more characteristics of the magnetic field in which it is disposed, wherein MPS 22 determines a location reading (e.g., a P&O reading) indicative of the PRS's position and orientation in the reference coordinate system.

Figure 2:
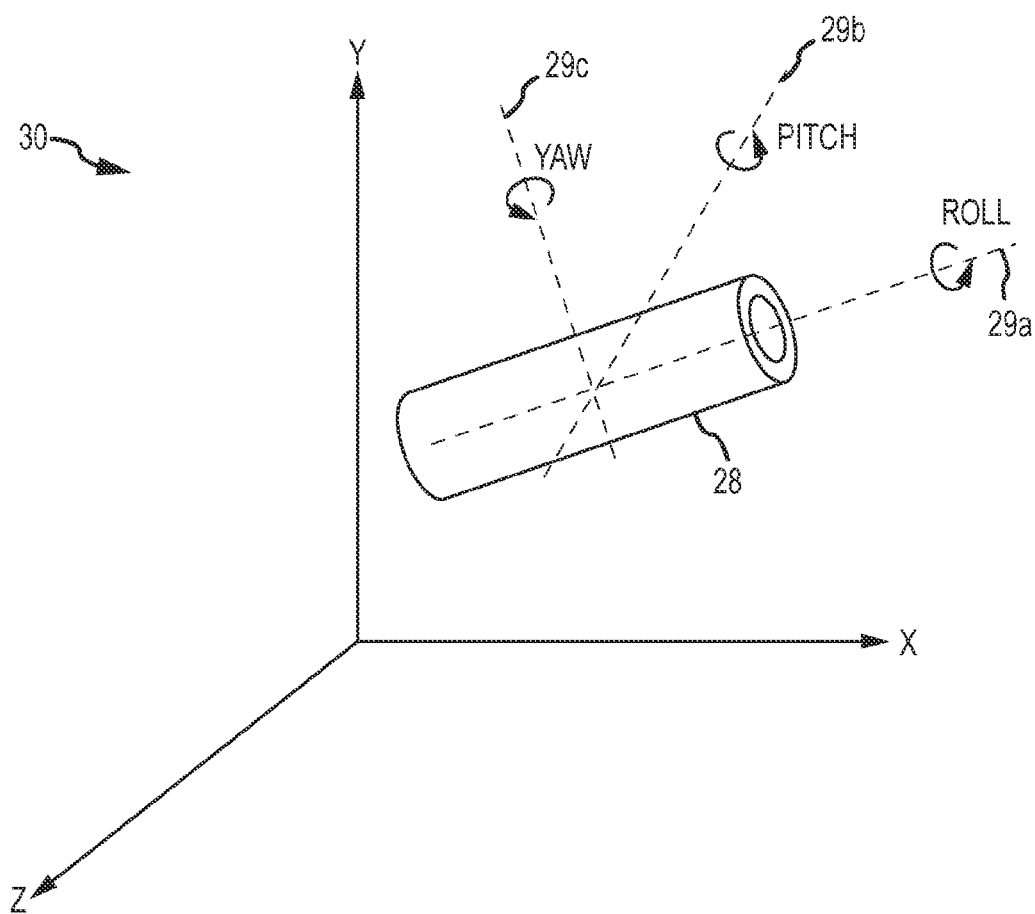
FIG. 2 is a diagrammatic view of an embodiment of a roll-sensing electromagnetic position sensor in the coordinate system of a medical positioning system.

FIG. 2 is a diagrammatic view of a roll-sensing position sensor 28 in the coordinate system 30 of MPS 22. Sensor 28 is illustrated as a tubular coil sensor. The position of sensor 28 can be determined by MPS 22 with respect to the three axes (X, Y, Z) of coordinate system 30 that are set relative to a piece of hardware, such as a magnetic field generator. The orientation angles (i.e., for roll, pitch, and yaw) of sensor 28 can also be determined by MPS 22, taken with respect to the origin. For a sensor with a coil wound about and extending along an axis, such as illustrated sensor 28, "roll" refers to rotation about the axis 29a along which the coil extends. "Pitch" and "yaw" respectively refer to rotation about axes that bisect the coil from the "top" (e.g., axis 29c) or "side" (e.g., axis 29b). A coil sensor with six DOF can sense rotation about all three axes. A sensor with five DOF generally can sense rotation about only two of the three orientation axes.

Figure 3:
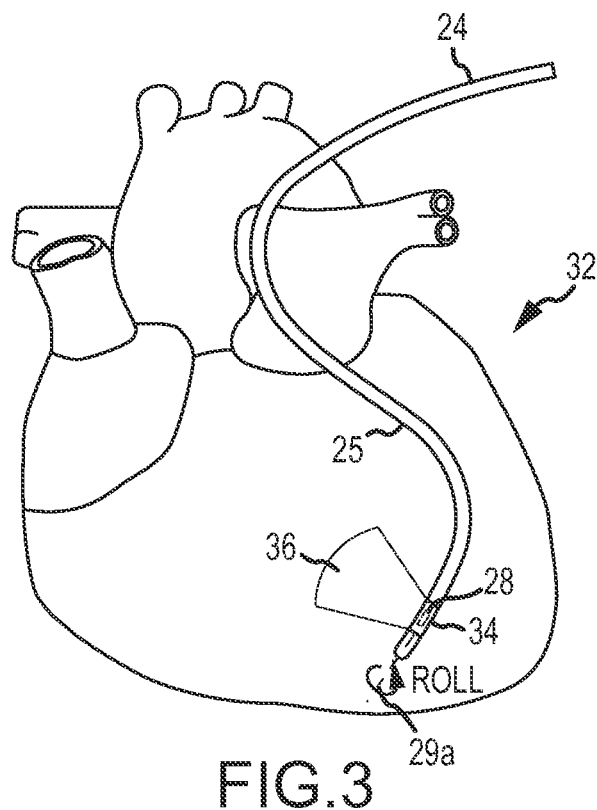
FIGS. 3 and 4 are diagrammatic views of an embodiment of a roll-sensing medical device disposed next to a human heart.
Figure 4:
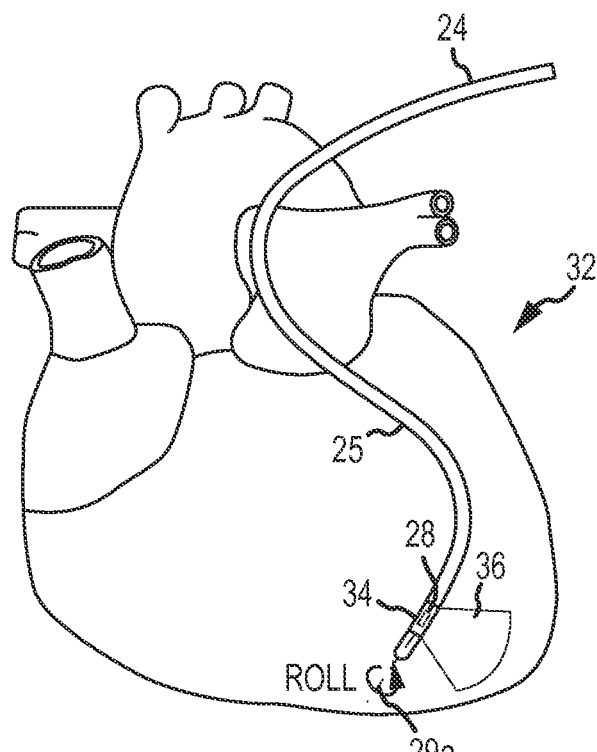

FIGS. 3 and 4 are diagrammatic views of an MPS-enabled medical device 24 disposed in a heart 32, in an exemplary system that can make use of roll detection. Medical device 24 is shown as an intracardiac echocardiography (ICE) catheter with an ultrasound transducer 34 having a field of view 36. Medical device 24 has a roll-sensing position sensor 28 (shown in phantom), generally similar to that described above, that is coaxial with an elongate body 25 of medical device 24. In other words, a longitudinal axis of sensor 28, similar to axis 29a shown in FIG. 2, may be substantially parallel with a longitudinal axis 29 of elongate body 25. Thus, the 3D position (X, Y, Z) and the 3D orientation (roll, pitch, yaw) of sensor 28 are also the 3D position and 3D orientation of the portion of medical device 24 containing sensor 28. Because sensor 28 is in substantially the same position in the elongate body 25 as transducer 34, the 3D position and 3D orientation of sensor 28 may also be the 3D position and 3D orientation of transducer 34.

In an exemplary application, medical device 24 may be an ICE catheter and may be used to acquire images of the walls of the heart, which may then be registered with a pre-acquired model of the heart. To capture the images, transducer 34 transmits ultrasound waves and receives reflections of the transmitted waves from within field of view 36. The reflections are used to construct an image of anatomical structures, medical devices, and other objects within field of view 36.

To register the ultrasound images with the pre-acquired model, it is advantageous to know the orientation of field of view 36, as described in U.S. Patent Application Publication 2009/0163810, entitled "Sensor Guided Catheter Navigation System", with inventors Kanade et al., hereby incorporated by reference in its entirety as though fully set forth herein. As described in Kanade, ultrasound images may be more easily registered with a model of the heart if field of view 36 is known precisely with reference to positioning system coordinate system 30. If the position and orientation of field of view 36 are known, the coordinates in coordinate system 30 of each pixel and/or structure in field of view 36 can be determined without using information from the ultrasound images themselves.

As illustrated in FIGS. 3 and 4, the medical device 24 may be rotated about longitudinal axis 29 between a first position (FIG. 3) and a second position (FIG. 4), for example. Accordingly, the orientation of field of view 36 can change simply by rotating transducer 34 about the axis 29 of medical device 24—i.e., the position (X, Y, Z), pitch, and yaw of transducer 34 may not change, while the roll of transducer 34 does change. In various embodiments, it may be desirable to detect such roll with fewer sensors, and by utilizing a reduced amount of space in medical device 24 with the sensor(s). A roll-sensing position sensor according one or more of the embodiments described herein may find use in such an application. It should be understood, however, that roll-sensing devices such as those described herein may be used in a wide variety of applications, with intracardiac imaging being just one such application.

Before proceeding to a description of roll-sensing position sensors and medical devices according to the present invention, a known position sensor will first be described to aid in understanding new design(s) for a roll-sensing position sensor or sensors.

Figure 5:
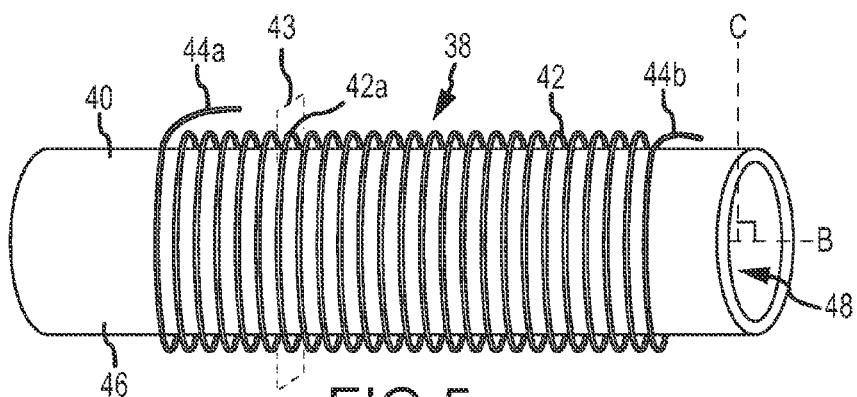
FIG. 5 is an isometric view of an electromagnetic position sensor known in the art.

FIG. 5 is an isometric view of a known electromagnetic positioning sensor 38. Sensor 38 includes a hollow sensor core 40 and a sensor coil 42 with two free ends 44a, 44b. Core 40 may be an elongated hollow tube extending along a central axis "B" having an outer surface 46 and a central through-bore 48 extending between opposing axial ends. Bore 48 is configured to allow sensor 38 to be threaded on or applied to medical devices. Radially-outermost surface 46 may act as a winding surface for coil 42. In turn, coil 42 may be wound on outer surface 46 about axis B with free coil ends 44 left exposed for use as leads in connecting coil 42 to a positioning system.

Sensor 38, like various embodiments described herein, may be configured to detect characteristics of a changing magnetic field. At the sensor level, such detection is represented by a current induced through coil 42 by a local magnetic field. The induced current is proportional to the change in magnetic flux passing through the coil. Such a flux change may occur as a result of one or both of (1) a changing flux of the magnetic field itself, or (2) a change in the projected area (i.e., position or orientation) of the coil in the field.

Briefly, the flux of the magnetic field itself may change according to the electrical signal provided in a field transmitting coil to create the magnetic field. As the current of the signal increases and/or decreases in amplitude (such as, for example, in a sinusoidal manner), the flux of the magnetic field changes. However, such flux changes in a medical environment will be accounted for by a processing system, such as by the MPS 22 shown in FIG. 1.

The projected area of a coil in a magnetic field is the rectilinear projection of a surface of the coil onto a plane normal to an axis of the field—that is, the two-dimensional area occupied by the volume of the coil in the normal plane. For example, if a circular coil is initially placed along an axis of a magnetic field (i.e., the normal vector of a loop of the coil is parallel with the field axis), the projected area of the coil on that axis of the field is simply the area of the circle. But as the circular coil is turned or tilted (i.e., about an axis similar to axis 29b or 29c shown in FIG. 2), each loop in the coil has a decreasing projection onto the plane normal to the field axis. As the projected area of the coil onto an axis of the field decreases, so does the magnetic flux passing through the coil on that axis. Once the coil is turned or tilted 90 degrees from its original position, such that its normal vector is perpendicular to the field axis, its projected area is essentially zero, as is the amount of flux passing through the coil.

Referring to FIG. 5, in general, a single loop in a tightly-wound coil may be substantially planar. That is, for example, loop 42a may lie substantially within a plane 43. Additionally, such a plane 43 may be substantially perpendicular to the longitudinal axis B of the coil 42. Electromagnetically, this perpendicularity may be problematic for magnetic field-based orientation detection because in-plane rotation (i.e., about a line perpendicular to the plane of the loop, such as the longitudinal axis B of the coil in the embodiment shown in FIG. 5) may not change the projected area of the loop in any axis of the magnetic field. As a result, the coil appears to a signal processing device (e.g., MPS 22 shown in FIG. 1) to have the same orientation despite rotation of the coil. Thus, in-plane rotation is not meaningfully detected by the coil. In other words, rotation about a line that is perpendicular to the plane of the loops in the coil is a rotational "blind spot". Various embodiments described herein address such rotational blind spots for magnetic position sensors.

With continued reference to FIG. 5, coil 42 is wound around core 40 such that each individual loop is effectively perpendicular to axis B. Axis B thus serves as a rotational blind spot for each loop in coil 42 and sensor 38 cannot detect rotation about axis B. In various embodiments described herein, rotation about axis B and the like is referred to as the "roll" of the sensor's orientation. Because the rotational blind spot of sensor 38 is coincident with roll axis B, sensor 38 cannot sense roll or is limited in its ability to sense roll.

A rotational blind spot for a loop of a coil may be determined by the winding (or lead) angle of the coil. As used herein, winding angle refers to the smallest angle between (1) a line tangential to a portion of a loop in the coil (such as, for example, loop 42a) when viewing the coil 42 from the side (i.e., a line in the plane 43 in which the loop 42a substantially sits), and (2) a line perpendicular to the longitudinal axis of the coil, shown as axis B and the like. Such a perpendicular line is represented in FIG. 5 and throughout the Figures as line "C". In sensor 38, each loop in the coil is parallel with line C. In sensor 38, therefore, coil 42 has a winding angle of substantially zero.

Figure 6A:
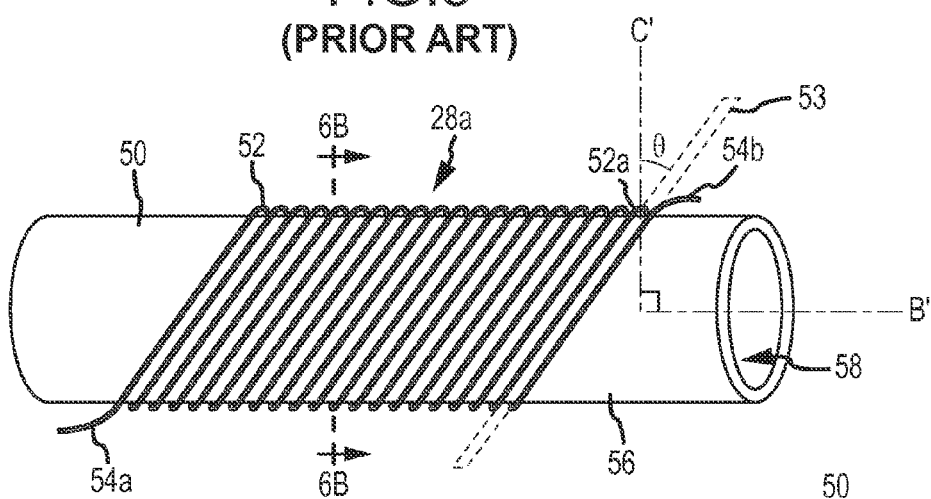
FIG. 6A is an isometric view of an embodiment of a roll-sensing electromagnetic position sensor.

FIG. 6A is an isometric view of a first embodiment of an electromagnetic position sensor, designated sensor 28a, that is configured to have a current induced therein for use in detecting roll or rotation about a longitudinal axis defined by at least a portion of sensor 28a. Sensor 28a may include a hollow sensor core 50 and a sensor coil 52 situated substantially in a plane 53 and with two free ends 54a, 54b. Core 50 may be an elongated hollow tube extending along longitudinal axis B' having an outer surface 56 and a central through-bore 58 extending between opposing axial ends. Bore 58 may be configured to allow sensor 28a to be threaded on or applied to medical devices, among other things. Radially-outermost surface 56 may act as a winding surface for coil 52. In turn, coil 52 may be wound on outer surface 56 about axis B' with free coil ends 54a, 54b left exposed for use as leads in connecting coil 52 to MPS 22. It should be noted that axis B' is shown superimposed outside the surface of core 50 to illustrate the intersection of axis B' with line C, discussed in more detail below. Axis B in fact extends through the geometric center of core 50 and of coil 52.

Core 50 may be solid or hollow (as shown), depending on the application, and may be made of, for example only, metal or polymer. Materials for core 50 may be selected for, among other things, their magnetic permeability to enhance the sensitivity of coil 52, or for the similarity of their mechanical properties to desired mechanical properties of a medical device. For example, a metal core may be desirable to increase sensitivity in a smaller-diameter device (e.g., for use in a guidewire application). Instead of a hollow core, a solid core may be used in an embodiment to reduce the size of the sensor and/or enhance the sensitivity of the sensor. Alternatively, the core may be omitted entirely (e.g., an air core). Core 50 may be sized, both radially and axially, to suit a particular application.

Figure 6B:
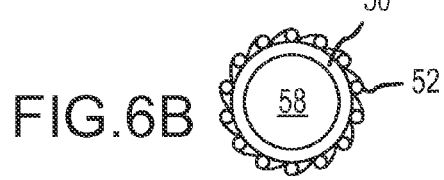
FIG. 6B is a cross-sectional view of the position sensor of FIG. 6A.
Figure 6C:
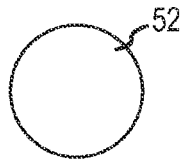
FIGS. 6C-6J are diagrammatic views of the various shapes that may be used for a loop in the sensor of FIG. 6A.
Figure 6D:
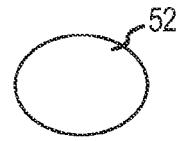
Figure 6E:
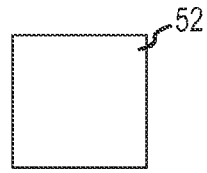
Figure 6F:
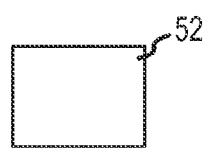

FIG. 6B is a cross-sectional view of sensor 28a, taken substantially along line 6B-6B, which is parallel with line C. As illustrated in FIGS. 6A and 6B, coil 52 may comprise a conductor wound to radially surround a volume. For example, coil 52 may comprise conventional wire having suitable characteristics, such as material or alloy type, thickness (wire gauge—AWG), insulative coating type and thickness, and the like, as known in the art. Coil 52 may be wound to a desired number of loops, desired axial length, and desired radial thickness (i.e., layers) to meet desired detection characteristics. Though only one layer is shown for coil 52, more layers may be included, in an embodiment. Coil 52 may alternatively or additionally comprise another conductor type, such as electrically-conductive traces on a flexible printed circuit board (shown in FIG. 8).

As shown in FIG. 6A, coil 52 has a substantially nonzero winding or lead angle $\theta$ relative to the perpendicular line C. Because the coil has a nonzero winding angle, a line perpendicular to a loop in coil 52 is offset from axis B', so the projected area of the coil in the magnetic field changes as sensor 28a rotates about axis B'. Because the projected area changes based on the rotation of the coil, the signal produced by sensor 28a responsive to the magnetic field is indicative of the roll of the sensor. But each loop in coil 52 is effectively parallel with each other loop, so sensor 28a still has a rotational blind spot. So although sensor 28a can detect roll, it remains a five-DOF sensor.

The winding angle $\theta$ of coil 52 may be varied in different embodiments to, e.g., maximize the sensor's ability to detect roll but still minimize the axial size of the sensor. The winding angle should be substantially nonzero—i.e., large enough that the projected area of the coil in the magnetic field meaningfully changes as the sensor rolls such that a processor or electronic control unit such as, for example only, MPS 22 shown in FIG. 1, can determine the roll of the coil 52 according to the change in projected area. The exact angle needed for such a "meaningful" change may vary depending on characteristics of the sensor (e.g., materials, coil diameter, etc.) and/or the system (e.g., magnetic field strength, signal processing resolution, signal-to-noise ratio). In one exemplary combination of sensor and system, the projected area of the coil in the magnetic field meaningfully changes with a winding angle $\theta$ of the coil 52 that is at least about 2 degrees. Accordingly, in an embodiment, a winding angle of coil 52 may be considered "substantially nonzero" if it is at least two degrees, though "substantially nonzero" is not necessarily limited to such an angle. In an embodiment, coil 52 may achieve maximum resolution for roll detection with a winding angle $\theta$ of about 45 degrees. Accordingly, in various embodiments, the winding angle $\theta$ may be between about 2 degrees and about 45 degrees. It should be understood that the foregoing winding angles are exemplary only, and not limiting in nature except as may be recited in the claims.

Figure 6G:
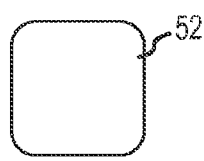
Figure 6H:
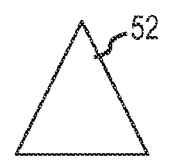
Figure 6I:
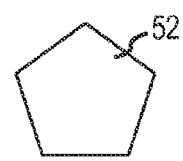
Figure 6J:
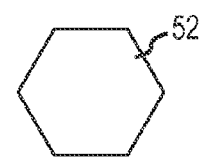

FIGS. 6C-6J are alternate diagrammatic views of exemplary exterior shapes of a loop in coil 52, such as loop 52a, viewed orthogonally to the plane in which the loop substantially sits (e.g., plane 53). As illustrated in the drawings, many different loop shapes may be used to wind coil 52 (though, generally, a single shape may be used for each loop in a single coil), and such shapes are contemplated. Each loop in coil 52 may be substantially in the shape of a circle (FIG. 6C, an oval (FIG. 6D, a square (FIG. 6E, a rectangle (FIG. 6F, a rectangle with rounded corners (FIG. 6G) a triangle (FIG. 6H), a pentagon (FIG. 6I), a hexagon (FIG. 6J), another convex polygon, or another shape not explicitly shown in the drawings. In a polygonal embodiment, each loop in coil 52 may have "sharp" edges (e.g., as illustrated in FIGS. 6E, 6F, and 6H-6J) or rounded edges (e.g., as illustrated in FIG. 6G). Also, the each loop in the coil 52 may exhibit radial, bilateral, or other symmetry, or may be asymmetric. Accordingly, the terms "loop" and "coil", as used herein, are not limited to round or circular shapes, but may one or more of a number of shapes.

Figure 7A:
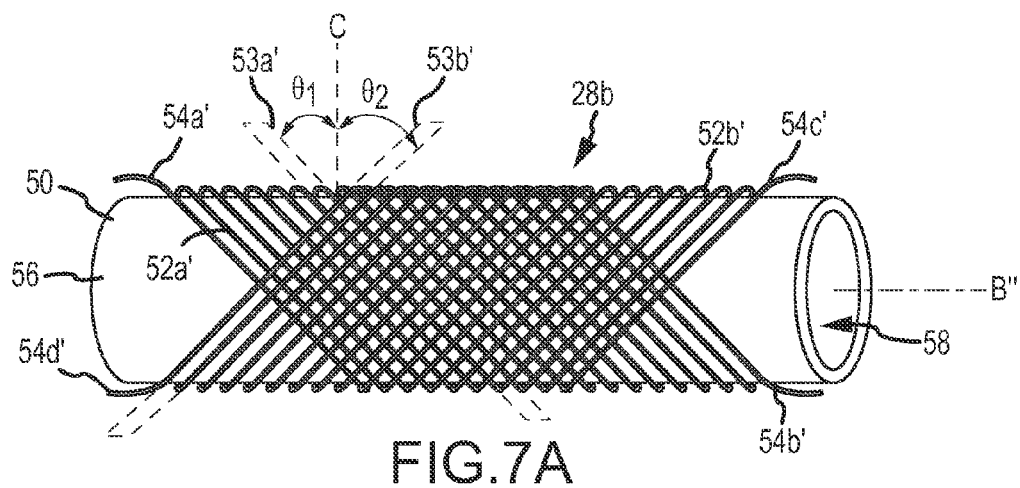
FIG. 7A is an isometric view of another embodiment of a roll-sensing electromagnetic position sensor.

FIG. 7A is an isometric view of another embodiment of a roll-sensing electromagnetic position sensor, designated sensor 28b. Sensor 28b includes many of the same materials, aspects, and features of sensor 28a, but sensor 28b has a coil 52' with two portions 52a', 52b', each with its own winding angle, labeled angles $\theta_1$ and $\theta_2$, respectively. Portion 52a' has free ends 54a', 54b', and portion 52b' has free ends 54c', 54d' for connection to MPS 22. Portion 52a' is wound directly on outer surface 56, and second portion 52b' is wound on top of—i.e., radially-outwardly of—first portion 52a'.

First portion 52a' and second portion 52b' may be formed from separate conductors. In such an embodiment, portion 52a' and portion 52b' produce independent signals indicative of each portion's respective P&O. Like sensor 28a, each portion 52a', 52b' can sense its own roll. Also like sensor 28a, each portion 52a', 52b' has a rotational blind spot. But a rotation about the blind spot of one of portions 52a', 52b' is detected by the other portion. As a result, the signals from portions 52a' and 52b' are collectively indicative of a full six degrees-of-freedom. The independent signals from portions 52a', 52b' can be processed (e.g., by MPS 22) to determine the six-DOF P&O of sensor 28b.

Figure 7B:
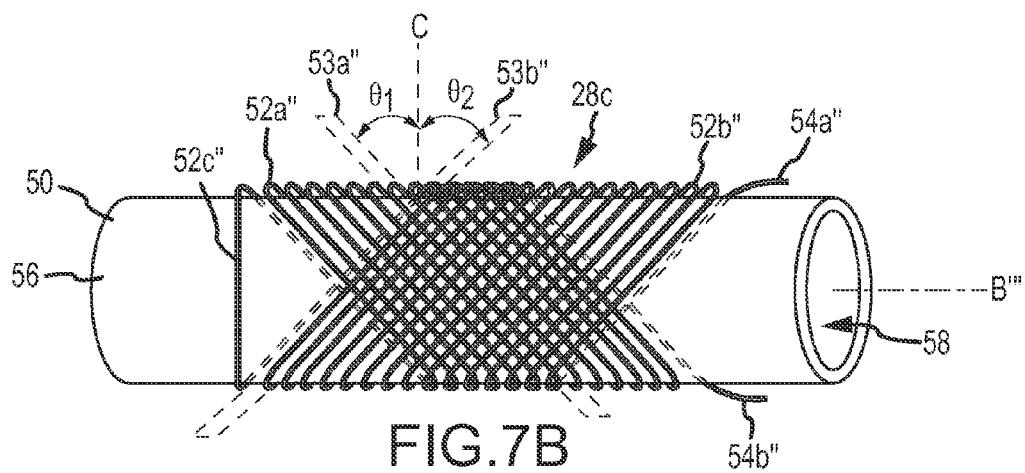
FIG. 7B is an isometric view of another embodiment of a roll-sensing electromagnetic position sensor.

FIG. 7B is an isometric view of another embodiment of a roll-sensing electromagnetic position sensor, designated sensor 28c. Sensor 28c is similar to sensor 28b in that portion 52a" is wound directly on outer surface 56 and second portion 52b" is wound on top of—i.e., radially-outwardly of—first portion 52a". But coil 52" is formed from a single continuous conductor, so first portion 52a" and second portion 52b" are electrically coupled together by a transition portion 52c" and produce a single signal indicative of the sensor's P&O. With two winding angles incorporated into a single continuous conductor, coil 52" has no rotational blind spot—rotation about any line causes a change in the projected area of some portion of the coil in the magnetic field. Thus, coil 52" can detect rotation about all rotational axes and the current induced in coil 52" is indicative of a full six degrees-of-freedom.

In either a single-conductor (sensor 28c, FIG. 7B) or a multi-conductor embodiment (sensor 28b, FIG. 7A), winding angles $\theta_1$ and $\theta_2$ may be varied in design and manufacturing for a particular application. At least one winding angle in coil 52 should be substantially nonzero—i.e., large enough that the projected area of the coil in the magnetic field meaningfully changes as the sensor rolls, as discussed above. For example, one or both of winding angles $\theta_1$, $\theta_2$ may be between about 2 degrees and about 45 degrees, inclusive. Coil 52 may achieve maximum resolution for roll detection in an embodiment in which the sum of $\theta_1$ and $\theta_2$ is approximately 90 degrees such that the first and second coil portions 52a, 52b are wound substantially perpendicular to each other. However, in an embodiment, one or more other winding angles in coil 52 may be substantially zero. $\theta_1$ and $\theta_2$ may be congruent—i.e., equal and opposed across line C—or incongruent. Furthermore, although first portion 52a and second portion 52b are shown as overlapping over most of their respective axial lengths, the amount of overlap may be varied as desired. In an embodiment, overlap may be eliminated such that portion 52a is axially adjacent to portion 52b. Portions 52a, 52b may be the same or different with respect to number of loops, axial length, and radial thickness (i.e., layers). In a multi-conductor embodiment, portions 52a, 52b may be the same or different with respect to conductor type, material or alloy type, thickness (wire gauge—AWG), and insulative coating type and thickness.

It should be understood that many variations may be made to the illustrated embodiments of sensors 28a, 28b, and 28c and remain within the scope and spirit of the claims. More than two conductor portions may be used, and the winding angles of those conductor portions may be completely unique from one another or may be redundant (i.e., the sensor can include multiple winding segments, each with its own winding angle). Winding angles $\theta$, $\theta_1$, and $\theta_2$ may be different from those explicitly set forth above. Further, coil 52 and coil portions 52a and 52b are not limited in number or pitch of loops insofar as the sensor maintains the features recited in the claims.

Figure 8:
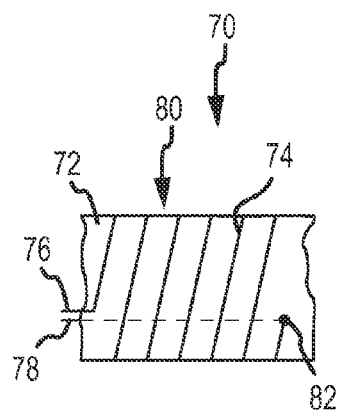
FIG. 8 is an isometric view of another embodiment of a roll-sensing electromagnetic position sensor.

FIG. 8 is an isometric view of a fourth embodiment of a roll-sensing position sensor, designated sensor 70. Sensor 70 comprises a flexible printed circuit board (PCB), as described in co-pending U.S. patent application Ser. No. 13/232,536, entitled "Method for Producing a Miniature Electromagnetic Coil Using Flexible Printed Circuitry", which is hereby incorporated by reference in its entirety as though fully set forth herein. A brief description of the flexible PCB of sensor 70 will be set forth below. The above-referenced application may be consulted for greater detail about the design and manufacture of flexible PCBs.

Sensor 70 includes an electrically insulative, relatively flexible substrate 72 and an electrically conductive trace 74 disposed (i.e., "printed") on a first surface of substrate 72. Trace 74 is arranged in a pattern configured to create a sensing coil 80 when the substrate 72 is folded or formed into the final shape shown. The shape formed with substrate 72 extends along an axis (similar to axis B', see FIG. 6A, and the like), about which coil 80 is disposed.

To achieve a desired final shape, substrate 72 may be wrapped, folded, or otherwise formed. In FIG. 8, the final, desired shape is a cylinder, having a circular shape in radial cross-section, formed by wrapping substrate 72 so that its ends meet to form a seam. It should be understood, however, that other shapes are possible (such as those shown in FIGS. 6C-6J). Before being formed into the final shape shown, substrate 72 may be generally rectangular in shape, having a longitudinal direction (i.e., long dimension) and a transverse direction (i.e., shorter dimension). It should be understood, however, that the substrate may take a wide range of shapes and sizes, depending upon the desired trace pattern and sensor final form.

Substrate 72 may comprise conventional materials known in the art for use in flexible printed circuitry, such as a flexible plastic material selected from the group comprising polyimide, polyetheretherketone (PEEK), polyester, polyethylene terephthalate or a combination thereof. In some embodiments, substrate 72 may comprise KAPTON® or MYLAR® material commercially available from E.I. du Pont de Nemours and Company. It should be understood that variations are possible. The electrically-conductive trace 74 may comprise an electrically conductive material, such as copper, although other electrically-conductive materials, such as platinum or gold, or combinations thereof (e.g., copper plated with platinum, gold, or silver) may be possible depending on the desired electrical characteristics. Conventional approaches and materials may be used for forming ("printing") a suitable pattern (trace 74) on substrate 72. Moreover, although not shown, an over-layer of electrically-insulating material may be disposed over the electrically conductive trace pattern 74.

Trace 74 includes a start lead 76 and an end lead 78, which leads are configured to provide a signal that is coupled to a positioning system. End lead 78 extends on the "back" of the substrate 72 and is electrically coupled to the portion of trace 74 on the "front" of the substrate 72 via a through-hole 82. Trace 72 is electrically continuous between the start and end leads 76, 78. It should be understood that "start" and "end" designations are exemplary only and not limiting in nature. As shown, the spacing between traces may be constant across the trace pattern.

Trace 74 is printed such that coil 80 has a non-zero winding angle θ when sensor 70 is shaped into its final form. As a result, the projected area of coil 80 in a magnetic field changes as sensor 70 rotates about its central axis (as noted above, similar to axis B and the like), so sensor 70 can sense roll. But because only one winding angle is incorporated into coil 80, coil 80 has a rotational blind spot and sensor 70 is a five-DOF sensor.

Many variations may be made to the illustrated embodiment of sensor 70 and remain within the scope and spirit of the claims. Two or more PCB conductor portions may be used, and the winding angles of those conductor portions may be completely unique from one another or may be redundant. Multiple PCBs (or one or more conductive trace layers separated from an adjacent conductive trace layer by an intervening electrically insulative layer) may be layered radially on one another, or may be placed axially-adjacent to one another. Winding angles may be different from those explicitly set forth above. Further, coil 80 is not limited in number or pitch of traces insofar as the sensor maintains the features recited in the claims.

Figure 9:
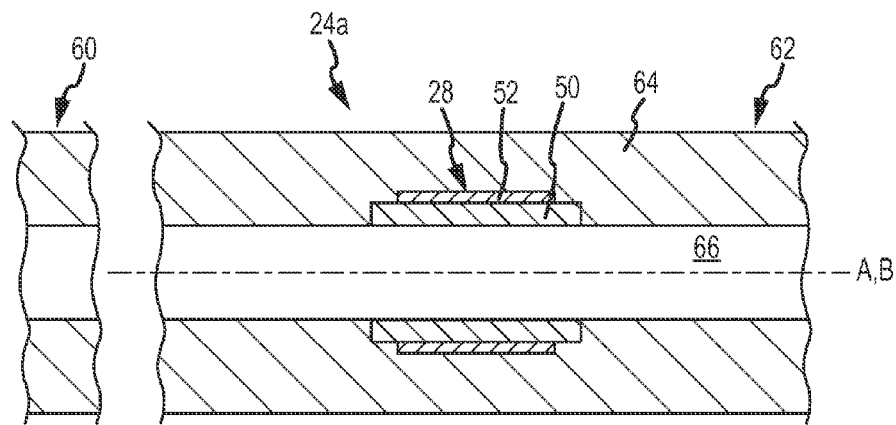
FIG. 9 is a cross-sectional view of an embodiment of a medical device with a roll-sensing electromagnetic position sensor.
Figure 10:
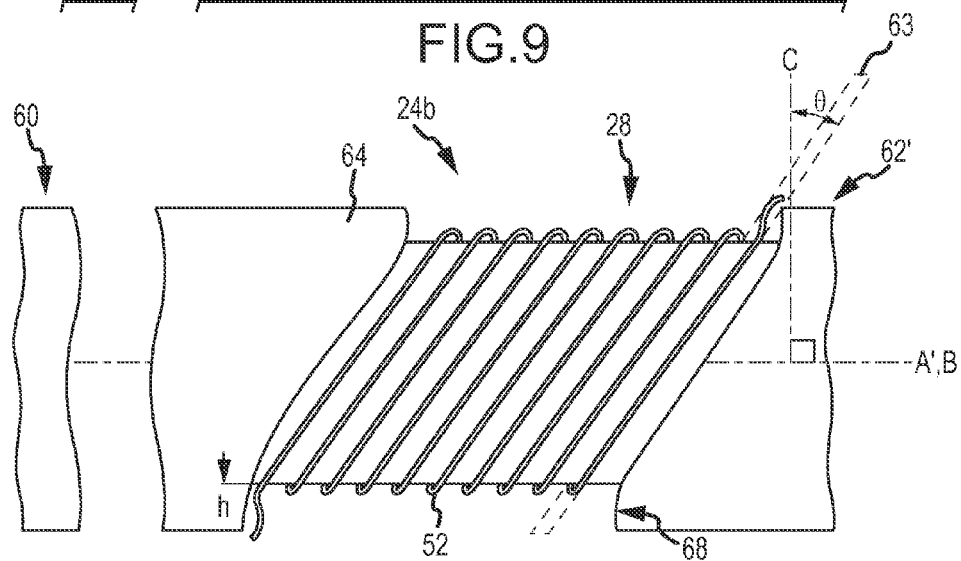
FIG. 10 is a side view of another embodiment of a medical device with a roll-sensing electromagnetic position sensor.
Figure 11:
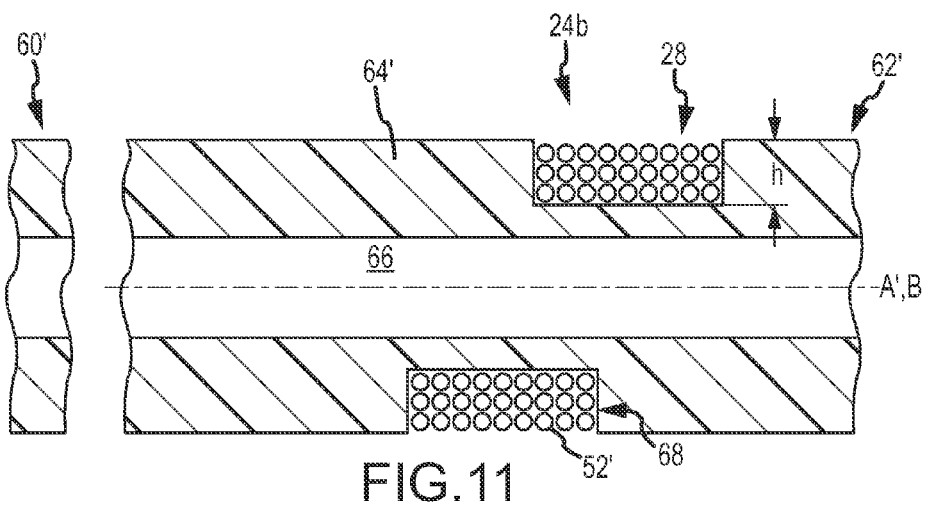
FIG. 11 is a cross-sectional view of a medical device similar to that of FIG. 10.

Roll-sensing position sensors such as sensors 28a, 28b, 28c, and 70 may find use in a variety of medical devices and may be incorporated into those devices in a variety of configurations. FIGS. 9-11 illustrate two such configurations. It should be understood, however, that other configurations are possible, and sensors 28a, 28b, 28c, and 70 are not limited to the medical device embodiments shown. In particular, it should be noted that the open central lumen provided by each sensor and the ability to scale the radial size of each sensor allows for the creation of telescoping medical devices, each of which may be independently tracked by a positioning system.

FIG. 9 is a side cross-sectional view of an embodiment of an MPS-enabled medical device 24a for use with system 10. Medical device 24a as shown includes a proximal end portion 60, a distal end portion 62, a shaft 64 and a central lumen 66 extending along a first axis "A". Medical device 24a further includes a medical device sensor 28, which itself includes a core 50 extending along a second axis B and a coil 52 disposed around axis B.

Shaft 64 may have a thickness, length, and cross-sectional shape as required for a particular application. Shaft 64 may be made of any suitable tubing material known in the art of medical instruments, such as engineered nylon resins and plastics, including but not limited to an elastomer commercially available under the trade designation PEBAX® from Arkema, Inc. of a suitable durometer, melting temperature and/or other characteristics. A lumen 66 (or multiple substantially parallel lumens) may be provided in shaft 64 for the passage of fluids, threading of other medical devices, or other purposes as known in the art Like shaft 64, lumen 66 may be shaped and sized to suit a particular application.

In the illustrated embodiment, sensor 28 has a hollow core 50 disposed around central lumen 66 and a coil 52 disposed about core 50 such that sensor axis B is coincident with device axis A. Because core 50 is hollow in the illustrated embodiment and placed around lumen 66, lumen 66 is clear and may be used for the passage of fluids, other medical devices, or other objects or materials as known in the art. Sensor 28 may be connected to a positioning system, such as MPS 22, via one or more wires (e.g., twisted-pair cable) extending proximally (not shown). Sensor 28 may be manufactured into medical device 24a according to methods known in the art such as, for example, as described in U.S. patent application Ser. No. 12/982,120, entitled "Electromagnetic Coil Sensor for a Medical Device", hereby incorporated by reference in its entirety as though fully set forth herein. Sensor 28 may also be created with a flexible printed circuit board (PCB).

FIG. 10 is a side view of another embodiment of a medical device with a roll-sensing electromagnetic position sensor, designated medical device 24b. Medical device 24b includes a proximal end portion 60, a distal end portion 62, and a shaft 64 with a wall and a circumferential groove 68 therein. A roll-sensing electromagnetic positioning sensor 28 is within groove 68. Shaft 64 extends along an axis A'.

In the illustrated embodiment, sensor 28 includes a coil 52 wound directly on groove 68 without a sensor core. The coil is wound about an axis B that is substantially coincident with device axis A'. Axes A' and B are shown projected over the surface of shaft 64 to illustrate their intersection with line C, but axes A' and B in fact extend through the radial center of the device. Coil 52 has a nonzero winding angle θ relative to line C—that is, a line tangent to a loop in coil 52 (such as, for example, a line in plane 63) meets line C at a nonzero angle so sensor 28 can sense roll about axis B, as described above in conjunction with FIGS. 2-8. It should be noted that medical device 24b is not limited to the sensor assembly shown in FIG. 9. In an alternate embodiment, sensor 28 may have multiple portions with multiple different winding angles. Coil 52 may be adapted to the desired geometry of device 24b by adjusting, e.g., the number of conductor portions and their winding angles, the number of axial windings, and the number of radial layers. Only one radial layer of coil 52 is shown in FIG. 10 for visual clarity, but a coil, such as coil 52', may include multiple radial layers, as shown in FIG. 11. Winding a sensor coil directly on a catheter shaft is described in greater detail in U.S. patent application Ser. No. 12/982,120, mentioned and incorporated by reference above.

Groove 68 provides a recess for sensor 28 so that medical device 24b may have a sensor integrated into shaft 64 without increasing the radial thickness of the device. The inner surface of groove 68 may serve as a winding surface onto which coil 52 may be directly wound. Groove 68 has a depth "h" and is bounded on its axial ends by sidewalls which form winding flanges. The sidewalls, though shown generally perpendicular to axis A', may have any angle and orientation required for a desired winding pattern. Similarly, the depth, width, and shape of groove 68 may be adapted to a desired winding pattern (e.g., number of conductor portions, winding angle(s), number of axial loops, number of radial layers).

As noted above, medical device 24b is not limited to the illustrated embodiment of sensor 28. In another embodiment, a coil without a core (i.e., air core) or a coil formed on a core (such as sensor 28a or 28b) may be used. A flexible PCB sensor may also be used. Groove 68 may be adapted in depth, width, sidewall angle, and otherwise in size and shape for a particular sensor and/or medical device.

FIG. 11 is a diagrammatic cross-sectional view of a medical device similar to that of FIG. 10, taken substantially in the plane of the page of FIG. 10. Shaft 64 has a central lumen 66 that extends along and is symmetric about device axis A'. Lumen 66 is separated from sensor 28 by a portion of the wall of shaft 64. Because sensor axis B is substantially coincident with medical device axis A', lumen 66 is also symmetric about axis B. Winding coil 52 in groove 68 allows for an unobstructed lumen 66 (or multiple substantially parallel lumens).

As noted above with respect to FIG. 10, the coil 52 in medical device 24b may include multiple radial layers. As shown in FIG. 11, the number of radial layers may be, for example only, three. Of course, more or fewer radial layers are possible and contemplated.

Figure 12:
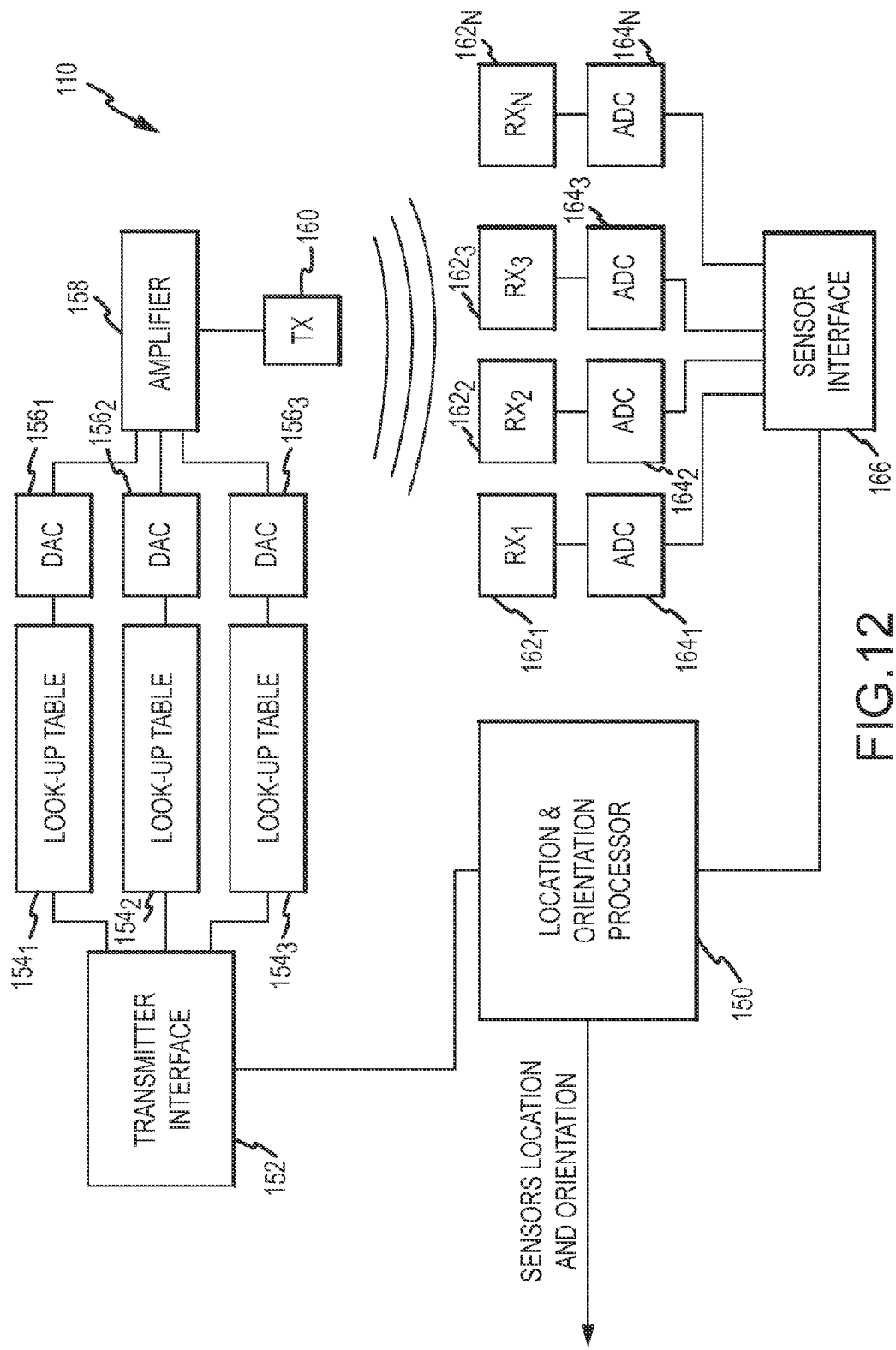
FIG. 12 is a schematic and block diagram view of an exemplary embodiment of a medical positioning system (MPS) as shown in block form in FIG. 1.

FIG. 12 is a schematic and block diagram of one exemplary embodiment of MPS 22, designated MPS 110, as also seen by reference to U.S. Pat. No. 7,386,339 entitled "Medical Imaging and Navigation System", hereby incorporated by reference in its entirety as though fully set forth herein, and portions of which are reproduced below, which generally describes, at least in part, the gMPS™ medical positioning system commercially offered by MediGuide Ltd. of Haifa, Israel and now owned by St. Jude Medical, Inc. It should be understood that variations are possible, for example, as also seen by reference to U.S. Pat. No. 6,233,476 entitled "Medical Positioning System", also hereby incorporated by reference in its entirety as though fully set forth herein. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated by reference in their entireties as though fully set forth herein. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. MPS sensors $162_1$, $162_2$, $162_3$ and $162_N$ may be sensors 28a, 28b, 28c, and/or 28d as described herein, or may be other sensors. Further, MPS sensors $162_1$, $162_2$, $162_3$ and $162_N$ may be incorporated into medical device 24a, medical device 24b, or another medical device. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A magnetic sensor assembly comprising:
    a coil extending along and disposed about an axis, said coil comprising one or more portions, each of said portions comprising at least one loop about a full circumference around said axis, each loop defining a winding angle, each loop within a given one of said portions defining the same winding angle as each other loop within said given portion such that each portion defines a winding angle, wherein at least one of said one or more portions defines a winding angle that is substantially nonzero relative to a line perpendicular to said axis, whereby a projected area of said coil in an applied magnetic field changes as said coil rotates about said axis, wherein each loop of at least one of said one or more portions comprises traces on a flexible printed circuit board.

2. The magnetic sensor assembly of claim 1, wherein said coil comprises at least two portions, wherein a first of said at least two portions defines a first winding angle that is substantially nonzero relative to said line, and a second of said at least two portions defines a second winding angle that is different from said first winding angle.

3. The magnetic sensor assembly of claim 2, wherein the sum of said first winding angle and said second winding angle is approximately 90 degrees such that said first portion and said second portion are substantially perpendicular.

4. The magnetic sensor assembly of claim 2, wherein said first portion is electrically coupled with said second portion.

5. The magnetic sensor assembly of claim 1, further comprising a core extending along said axis having a core outer surface, wherein said coil is disposed on said core outer surface.

6. The magnetic sensor assembly of claim 1, wherein an exterior shape of a loop of said coil substantially comprises a shape selected from the group consisting of:
circle;
oval; and
convex polygon.

7. The magnetic sensor assembly of claim 1, wherein at least one of said one or more portions comprises electrically-conductive wire.

8. The magnetic sensor assembly of claim 1, wherein said coil radially surrounds a volume through which said axis extends.

9. A medical device comprising:
a sensor assembly comprising:
a hollow core extending along an axis and having an outer surface; and
a coil extending along and disposed about said axis, the coil comprising a first portion, disposed on said core outer surface, comprising at least one first loop about the full circumference of said axis, said at least one first loop defining a first winding angle, and a second portion, electrically coupled with said first portion, comprising at least one second loop about the full circumference of said axis, said at least one second loop defining a second winding angle that is different from said first winding angle, wherein at least a part of said second portion overlaps at least a part of said first portion;
wherein at least one of said first winding angle and said second winding angle is substantially nonzero relative to a line that is perpendicular to said axis;
whereby said coil is configured to produce a signal responsive to an applied magnetic field indicative of at least the roll of said coil about said axis.

10. The medical device of claim 9, wherein the sum of said first winding angle and said second winding angle is approximately 90 degrees such that said first portion and said second portion are substantially perpendicular.

11. The medical device of claim 9, wherein one of said first winding angle and said second winding angle is substantially zero relative to said line that is perpendicular to said axis.

12. The medical device of claim 9, wherein at least a part of said second portion is radially-outward of at least a part of said first portion.

13. The medical device of claim 9, wherein at least a part of said second portion is axially adjacent to at least a part of said first portion.

14. The magnetic sensor assembly of claim 1, further comprising a second one of said one or more portions, said second portion comprising traces on said flexible printed circuit board that are different from said traces comprising said first portion.

15. The magnetic sensor assembly of claim 1, wherein said flexible printed circuit board is a first flexible printed circuit board, further comprising a second portion of said one or more portions, said second portion comprising traces on a second flexible printed circuit board.

16. The medical device of claim 9, further comprising an elongate shaft, wherein said sensor assembly is disposed in said shaft.

17. An elongate medical device comprising:
an elongate shaft defining a longitudinal shaft axis; and
a sensor assembly disposed within said elongate shaft and comprising:
a core extending along a core axis that is parallel with said longitudinal shaft axis and having an outer surface; and
a coil extending along and disposed about said core axis, the coil comprising a first portion, disposed on said core outer surface, comprising at least one first loop about the full circumference of said axis, said at least one first loop defining a first winding angle, and a second portion, comprising at least one second loop about the full circumference of said axis, said at least one second loop electrically coupled with said first portion, defining a second winding angle that is different from said first winding angle;
wherein at least one of said first winding angle and said second winding angle is substantially nonzero relative to a line that is perpendicular to said core axis and wherein at least a part of said second portion overlaps at least a part of said first portion.

18. The elongate medical of claim 17, wherein the sum of said first winding angle and said second winding angle is approximately 90 degrees such that said first portion and said second portion are substantially perpendicular.

19. The elongate medical device of claim 17, wherein one of said first winding angle and said second winding angle is substantially zero relative to said line that is perpendicular to said core axis.

20. The elongate medical device of claim 17, wherein at least a part of said second portion is radially-outward of at least a part of said first portion.

21. The elongate medical device of claim 17, wherein at least said part of said second portion is positioned at a same longitudinal location of said core axis as at least said part of said first portion.

22. The magnetic sensor assembly of claim 5, wherein:
said core is a hollow core; and
said flexible printed circuit board radially surrounds said core outer surface of said hollow core and said flexible printed circuit board extends along said axis.

* * * * *